US012678463B2

(12) United States Patent
Loog et al.

(10) Patent No.: US 12,678,463 B2
(45) Date of Patent: Jul. 14, 2026

(54) ACTIVATED MESENCHYMAL STEM CELLS FOR TREATING LIMB ISCHEMIA

(71) Applicants: Cellin Technologies OÜ, Tallinn (EE); Taastava Kirurgia Kliinik AS, Tallinn (EE)

(72) Inventors: Andrus Loog, Keila (EE); Jekaterina Kazantseva, Tallinn (EE); Olavi Vasar, Kangru (EE); Tiit Meren, Ilmandu küla (EE); Triin Vasar, Peetri alevik (EE); Mart Raik, Tallinn (EE)

(73) Assignee: Cellin Technologies OÜ, Tallinn (EE)

( * ) Notice: Subject to any disclaimer, the term of this patent is extended or adjusted under 35 U.S.C. 154(b) by 1180 days.

(21) Appl. No.: 17/636,228

(22) PCT Filed: Aug. 27, 2019

(86) PCT No.: PCT/IB2019/057182
§ 371 (c)(1),
(2) Date: Feb. 17, 2022

(87) PCT Pub. No.: WO2021/038275
PCT Pub. Date: Mar. 4, 2021

(65) Prior Publication Data
US 2022/0347223 A1      Nov. 3, 2022

(51) Int. Cl.
*A61P 9/10* (2006.01)
*A61K 35/28* (2015.01)
*C12N 5/0775* (2010.01)

(52) U.S. Cl.
CPC ............ *A61K 35/28* (2013.01); *C12N 5/0667* (2013.01); *C12N 2501/999* (2013.01)

(58) Field of Classification Search
None
See application file for complete search history.

(56) References Cited

FOREIGN PATENT DOCUMENTS

WO          2019146131 A1      8/2019

OTHER PUBLICATIONS

Lovasova, Veronika, et al. "Animal experimental models of ischemic limbs—A systematic review." Vascular Pharmacology 153 (2023): 107237. (Year: 2023).*

Baranovskii, Denis S., et al. "Adverse events, side effects and complications in mesenchymal stromal cell-based therapies." Stem cell investigation 9 (2022): 7. (Year: 2022).*
Acar, Rezzan D., Muslum Sahin, and Cevat Kirma. "One of the most urgent vascular circumstances: Acute limb ischemia." Sage Open Medicine 1 (2013): 2050312113516110. (Year: 2013).*
Nicpon, J., et al. "The effect of metamizole and tolfenamic acid on canine and equine adipose-derived mesenchymal stem cells (ASCs) an in vitro research." Polish Journal of Veterinary Sciences 18.1 (2015). (Year: 2015).*
Anjan Kumar Das, et al: Intra-arterial Allogeneic Mesenchymal Stem Cells for Critical Limb Ischemia are Safe and Efficacious: Report of a Phase I Study: World J Surg: 2013: 37: pp. 915-922.
ISR Written Opinion for International Application PCT/IB2019/057182 mailed Jun. 12, 2020.
Written Opinion for International Application PCT/IB2019/057182 mailed Jun. 12, 2020.
J. Nicpoń, etal.: The effect of metamizole and tolfenamic acid on canine and equine adipose-derived mesenchymal stem cells (ASCs) an in vitro research. Polish Journal of Veterinary Sciences vol. 18, No. 1 (2015), pp. 3-11.
Anjan Kumar Das et al.: Intra-arterial Allogeneic Mesenchymal Stem Cells for Critical Limb Ischemia are Safe and Efficacious: Report of a Phase I Study. World J Surg 37, pp. 915-922 (2013).
Andrea Augello, et al.: Mesenchymal Stem Cells: A perspective from in vitro cultures to in vivo migration and niches: European Cells and Materials: vol. 20: 2010: pp. 121-133.
Y. Shi, et al.: Mesenchymal stem cells: a new strategy for immunosuppression and tissue repair. Cell Res 20, pp. 510-518 (2010).
S. Ma, et al.: Immunobiology of mesenchymal stem cells. Cell Death Differ 21, pp. 216-225 (2014).
X. Wei, et al.: Mesenchymal stem cells: a new trend for cell therapy. Acta Pharmacol Sin 34, pp. 747-754 (2013).
L. Norgren et al.: on behalf of the TASC II Working Group. Inter-Society Consensus for the Management of Peripheral Arterial Disease (Tasc II). vol. 45, Issue 1, Supplement , pp. S5-S67, Jan. 1, 2007.
Zhaokang Cheng, et al.: Targeted migration of mesenchymal stem cells modified with CXCR4 gene to infarcted myocardium improves cardiac performance. Mol. Ther. 2008: 16: pp. 571-579.

* cited by examiner

*Primary Examiner* — Anoop K Singh
*Assistant Examiner* — Constantina E Stavrou
(74) *Attorney, Agent, or Firm* — LADAS & PARRY LLP

(57) ABSTRACT

A method for treating limb ischemia in a patient in need of such treatment by administering metamizole treated mesenchymal stem cells to the patient. The method provides a pharmaceutical product for angiogenesis growth to replace occluded blood vessels for avoiding limb amputation. Secretion of angiogenic growth factors VEGFA, HGF, bFGF, TEK are stimulated and the levels of pro-inflammatory cytokines IF6, CXCF8, CCF2, IL1-RN are reduced by activation of mesenchymal stem cells (MSCs). According to treatment results, MSCs produce proteins and signaling molecules for new blood vessel growth that accelerate the growth of new arteries.

6 Claims, 13 Drawing Sheets

ACTIVATED MESENCHYMAL STEM CELLS FOR TREATING LIMB ISCHEMIA

RELATED APPLICATION

Figure 1:
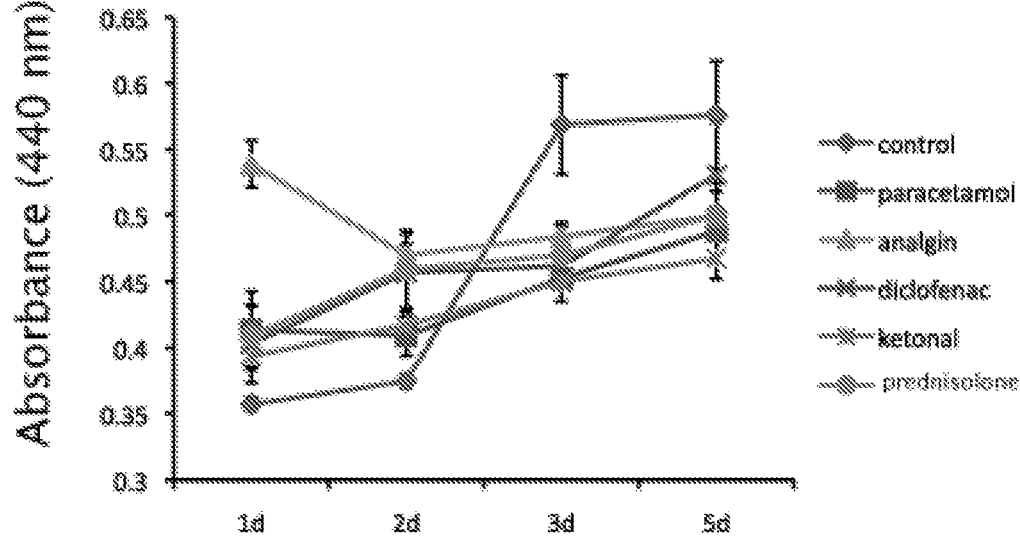

This is an application under 35 U.S.C. 371 of International Application No. PCT/IB2019/057182 filed on 27 Aug. 2019, the disclosure of which is incorporated in its entirety by reference herein.

FIELD OF THE INVENTION

Progress and success of the cell therapy is dependent of technologies that enable us to manipulate stem cells by stimulation of proliferation, differentiation and integration into regenerating tissues and organs. Isolated stem cells can be manipulated at different stages of cell therapy procedures including cell isolation, cell propagation, conditioning for transplantation and post grafting. The present invention relates to the use of clinically approved anti-inflammatory drugs to modulate activity of mesenchymal stem cells isolated from the adipose tissue. Modulation of secretion of different growth factors including angiogenic factors and cytokines as well as modulation of metabolic activity can be used to develop efficient MSC based pharmaceutical products for treatment of variety of health conditions.

BACKGROUND

Mesenchymal stem cells (MSCs) are characterized by their ability to differentiate into variety of cell lineages in vitro and to have immunomodulatory function in regenerative processes (Augello & De Bari, 2010), (Shi et al., 2010). Unlike pharmaceutical treatments that deliver particular active component at a specific dose, MSCs exert therapeutic effects by secreting various bioactive compounds in response to external stimulation (Ma et al., 2014). The soluble factors produced by MSCs are involved in anti-inflammatory and neovascularisation processes with profound effects on tissue injury and regeneration. Among diseases that can be treated using MSCs are for example immune and non-immune disorders such as myocardial infarction, diabetes, graft versus host disease, and liver cirrhosis (Wei et al., 2013) (Shi et al., 2010). Understanding the immunomodulatory properties of MSCs and ways how inflammatory microenvironment affects their function is of immense importance for developing better strategies to increase therapeutic efficiency of MSCs with a goal to create local and/or systemic conditions to stimulate healing and tissue regeneration.

Peripheral arterial disease is a condition characterized by restricted supply of oxygen and glucose due to malfunction of blood vessels. Peripheral vascular disease commonly affects arteries and in most advanced stages causes critical limb ischemia (CLI). Up to date, the most common therapeutic options include pharmacological treatments and surgery (Norgren et al., 2007), (Hamdy et al., 2013), (Cull et al., 2014). Non-steroidal anti-inflammatory drugs and synthetic glucocorticoid injections are widely used to reduce pain and inflammation of CLI patients. However, in many cases the result of the disease progression is gangrene and limb amputation. Development of new advanced therapies could improve clinical outcome and increase the life standard of patients. The clinical potential of MSCs for the treatment of ischemic conditions has been described in several animal models and early-phase human clinical trials (Liew & O'Brien, 2012). The efficiency and safety of administration of MSCs for treatment of acute ischemic disorders show great potential. Therapeutic efficiency of MSCs depends on their ability to provide immunomodulatory and angiogenic factors to suppress inflammation and stimulate angiogenesis. Non-activated MSCs express low levels of immunosuppressive factors, but the local conditions at the site of injections affect their functionality. To improve the therapeutic effect of MSCs, different strategies have been developed. The stimulation of MSCs by IFNγ or TNFα has been used to induce the secretion of immunomodulatory factors (Crop et al., 2010). Also, overexpression of CXCR4 in MSCs results in more effective homing of MSCs into ischemic tissue compared to unmodified cells (Cheng et al., 2008). Thus, immunosuppressive and angiogenic effects of MSCs could be stimulated by changing the conditions in the affected/diseased tissue or pretreatment of MSCs prior the grafting. Since patients with limb ischemia are treated with different anti-inflammatory drugs, the understanding of the consequences of these drugs on the anti-inflammatory and angiogenic function of MSCs is extremely important. The majority of NSAIDs function through the blockade of prostaglandin synthesis by inhibition of cyclooxygenase enzyme. Prostaglandin PGE2 is known to be one of the important compounds secreted by MSCs that is responsible for modulation of inflammation. However, the effect of NSAIDs on complex of metabolic responses and secretion of anti-inflammatory and angiogenic factors in MSC anti-inflammatory therapy is not known. The effect of NSAIDs (paracetamol, metamizole (Analgin™), ketoprofen and diclofenac) and glucocorticoid prednisolone, used in clinical practice to treat ischemic disorders, at therapeutic doses on cell cycle, metabolic activity, as well as on expression of angiogenic and inflammatory cytokines by AdMSCs has been analysed and will be described hereinafter.

SUMMARY OF THE INVENTION

The object of this invention is to provide a pharmaceutical product for angiogenesis growth to replace occluded blood vessels for avoiding limb amputation.

The inventors have developed protocols to stimulate mesenchymal stem cells to secret regulators that affect regeneration in ischemic limb and improve neo-vasculogenesis and arteriogenesis. Treatment of MSCs with metamizole (Analgin™), which active ingredient is metamizole, changes cell cycle, stimulates synthesis of angiogenic trophic factors VEGF, HGF, TEK and bFGF, reduces expression of inflammatory cytokines and chemokines such as IL6, IL1RN, CCL2, IL8/CXCL8.

Using rat models of limb ischemia shows that treatment of MSCs by metamizole (Analgin™) prior to transplantation stimulates neo-vasculogenesis and arteriogenesis of the operated limb.

According to following study examples, AdMSCs are perspective and promising cell source for cellular therapy to treat critical limb ischemia (CLI). Despite the promising preliminary studies of the application of MSCs for treatment of CLI patients, the MSCs potential is not very effective and many questions arise about their feasible use in clinics. Recently, it was shown that MSCs conditioning and pre-activation considerably improves their immunologic and therapeutic potential. The invention proposes a new strategy for treatment of CLI by pre-activation of AdMSCs by NSAID metamizole (Analgin™). The priming of AdMSCs by metamizole affects the proliferation and metabolic activity of AdMSCs, changes cell cycles, dynamically modulates expression profile of inflammatory cytokines and chemokines and induces expression of angiogenic markers, important in the context of the treatment of the disease. Preclinical experiments on rats demonstrated that activated by metamizole (Analgin™) AdMSCs were more effective for their therapeutic applications to treat limb ischemia by their accelerated and reliable neoarteriogenesis and neoangiogenesis.

In the present invention, secretion of angiogenic growth factors VEGFA, HGF, bFGF, TEK are stimulated and the levels of pro-inflammatory cytokines IL6, CXCL8, CCL2, IL1-RN are reduced by activation of mesenchymal stem cells (MSCs).

The invention provides metamizole treated mesenchymal stem cells for treating limb ischemia of a human patient. The pharmaceutical product of this invention comprises metamizole treated mesenchymal stem cells. The product is in injectable form and preferably comprises 1 million cells per kg of a patient. The cells are administered in an amount of 0.75-1.5 million per kg of body weight of a patient. Metamizole treated cells are in micro concentrations.

The invention also discloses a method of producing the product comprising metamizole treated mesenchymal stem cells. The method comprises following steps:

collecting fat tissue separation of mesenchymal stem cells from fat tissue reproduction of MSC-s influencing MSC-s with an active ingredient According to studies, treating MSCs with metamizole provides advantages and presumptions for the product to be effective.

As a result of the treatment, MSCs produce proteins and signalling molecules for new blood vessel growth that accelerate the growth of new arteries. The effects of different drugs on MSCs and the drug, metamizole, used in present invention has been studied and will be described hereinafter. The product of this invention has been successfully tested on animals.

Stem cells are already known to be involved in neoangiogenesis and neoarteriogenesis, and the aim of previous laboratory studies and animal experiments was to find the most effective cellular drug combination. As time is crucial for patients with critical leg ischemia, it is important to find a cellular drug that works as quickly as possible. Although the product of this invention is so far tested only on animals, according to prior art, it is believed to have the same effect on human patients.

FIGURES

The accompanying figures show following:

FIG. 1. WST metabolic activity assay of MSCs treated with anti-inflammatory drugs (AIDs).

The absorbance was measured at 440 nm after 2 hours of incubation with WST-1 reagent for control and AIDs-treated (paracetamol, metamizole (Analgin™), diclofenac, ketoprofen, prednisolone) AdMSCs. AdMSCs metabolic activity was measured at 1, 2, 3 and 5 days after the treatments.

Figure 2:
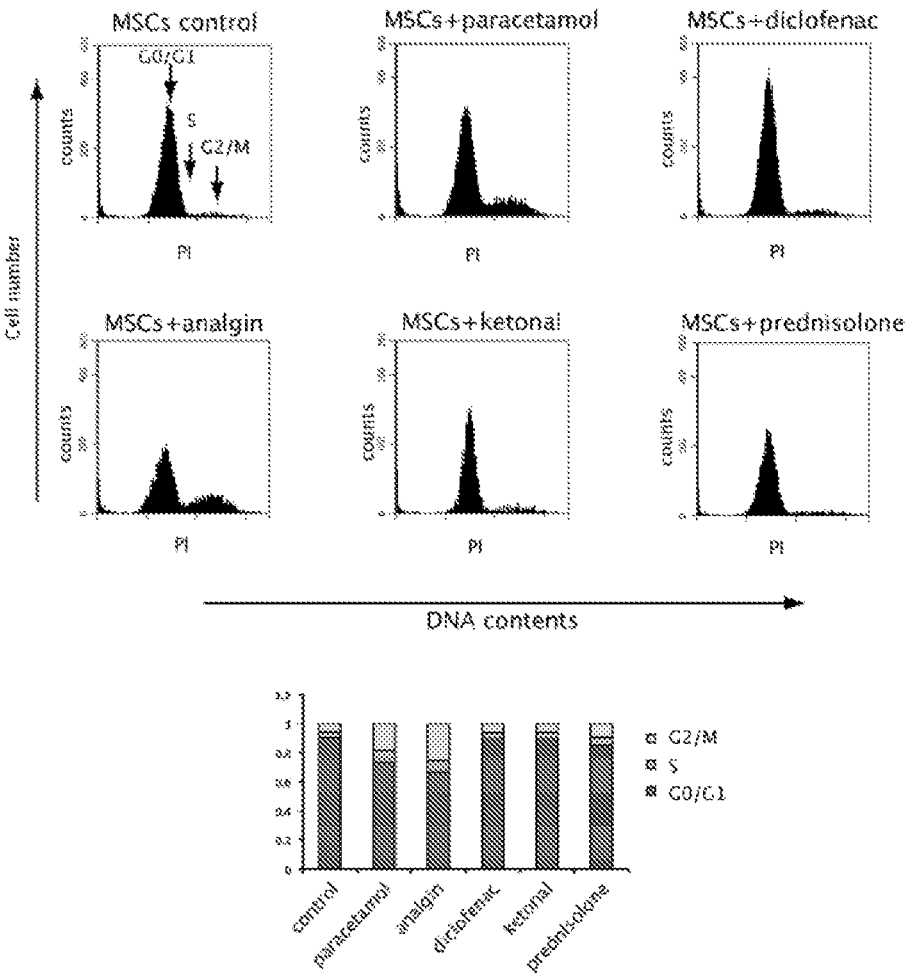

FIG. 2. Cell cycle analysis of control and AIDs-treated AdMSCs. AIDs-treated and control AdMSCs were stained with propidium iodide (PI) 24 h after treatments and analyzed using flow cytometry by BD Accuri C6.

Figure 3:
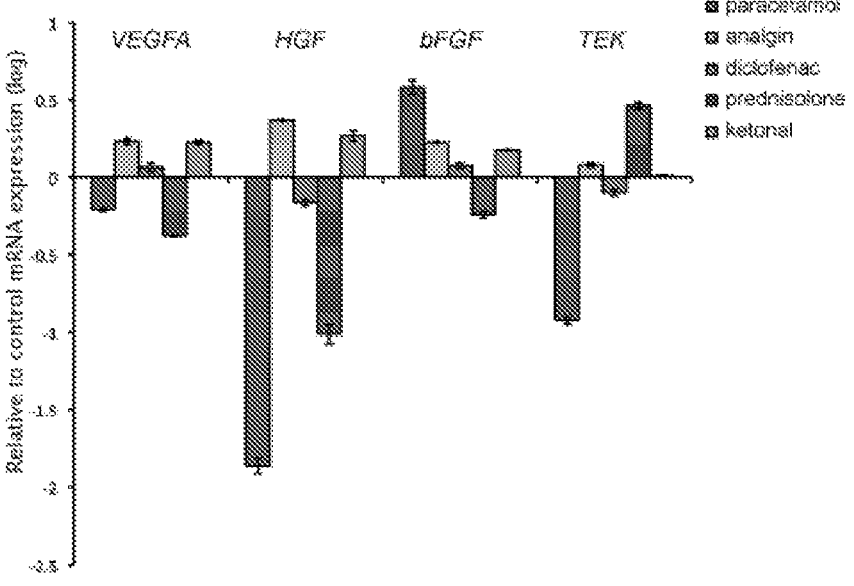

FIG. 3. Effects of AIDs on angiogenic markers expression in AdMSCs.

VEGFA, HGF, bFGF and TEK mRNA expression levels in AdMSCs treated with AIDs for 24 h were measured in triplicates by RT-qPCR and normalized with GAPDH mRNA expression levels. Data from AIDs-treated cells were calculated relatively to control untreated AdMSCs and results are represented in a log scale. Positive values indicated increased and negative values decreased mRNA levels compared to control untreated cells.

Figure 4:
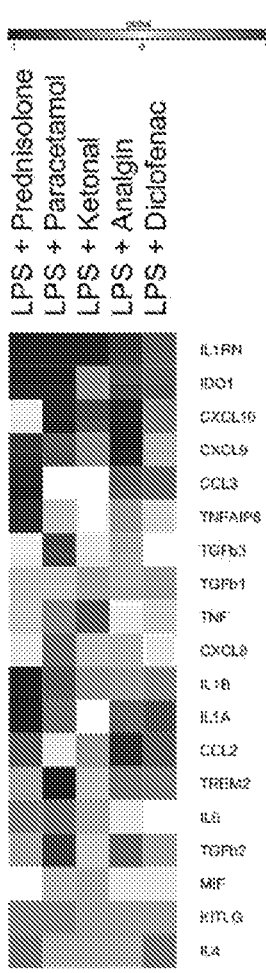

FIG. 4. Relative mRNA expression of inflammatory genes in LPS-stimulated and AIDs-treated for 24 h AdMSCs represented as heat map. Expression levels were measured in triplicates by RT-qPCR and normalized with GAPDH mRNA expression levels. Data from LPS-stimulated AIDs-treated AdMSCs were calculated as a relative fold difference compared to LPS-treated cells and converted to the log scale. The quantitative changes in gene expression are represented by shading: darker shade indicates up-regulation, whereas lighter shade indicates down-regulation. Expression data were visualized using GENE-E software.

Figure 5:
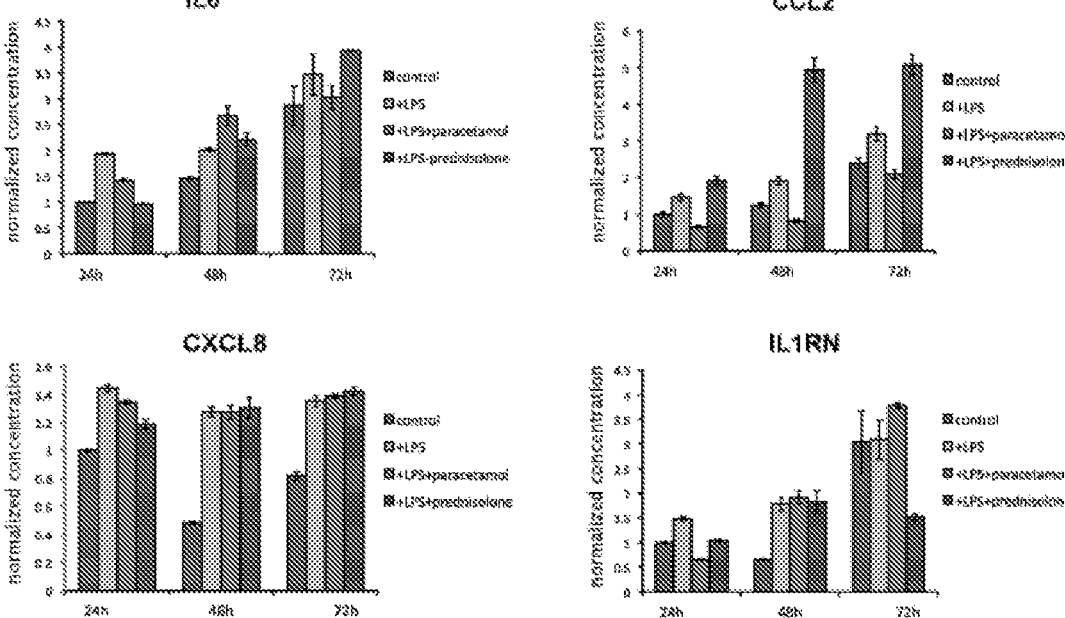

FIG. 5. Changes of inflammatory factors in culture media. Secreted IL6, CXCL8, CCL2 and IL1RN levels were measured from the conditional media of control, LPS-stimulated, and LPS-stimulated and paracetamol or prednisolone-treated AdMSCs by ELISA at 24, 48 and 72 h and represented as normalized to control 24 h probe.

Figure 6:
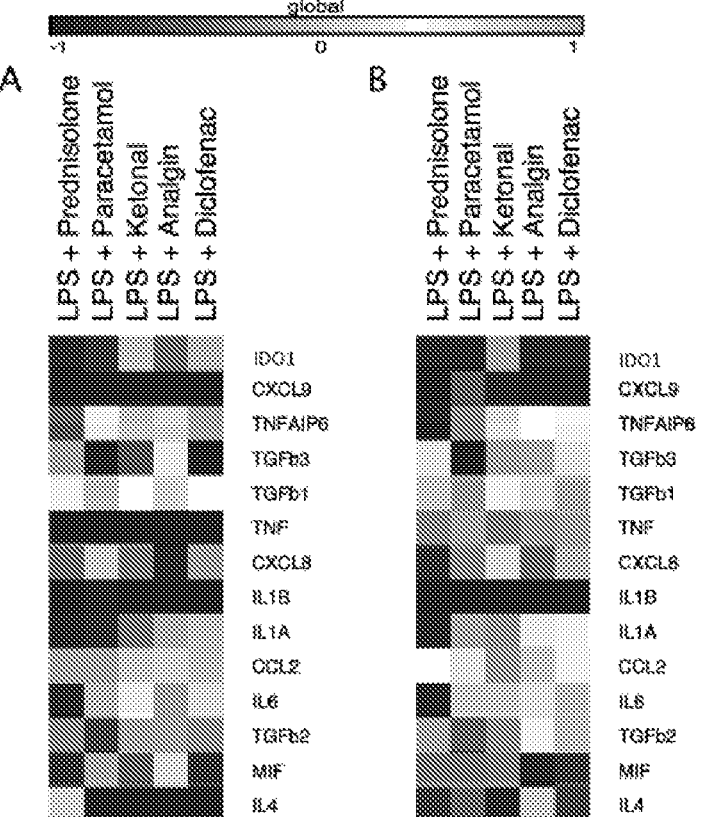

FIG. 6. Heat map of the expression profile of inflammatory genes in LPS-stimulated and AIDs-treated AdMSCs. Inflammatory genes mRNA expression levels of LPS-stimulated and AIDs-treated for 48 h (A) and 72 h (B) AdMSCs were calculated as a fold difference compared to LPS-treated AdMSCs and represented as heat maps. Expression levels of inflammatory gene mRNAs were measured in triplicates by RT-qPCR, normalized with GAPDH mRNA levels and converted to the log scale. Positive values (darker shade) indicate higher expression, and negative values (lighter shade) lower expression relatively to the control LPS-treated AdMSCs.

Figure 7:
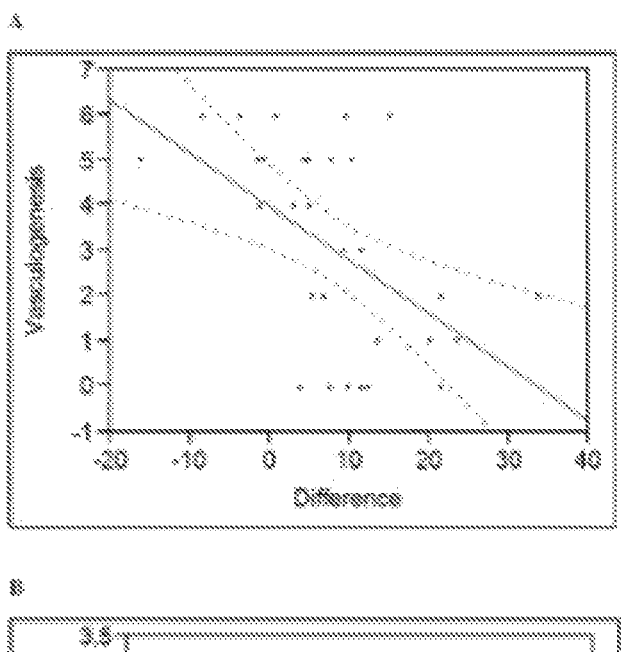

FIG. 7. Correlation analysis between angiography and perfusion difference. (A) shows vasculogenesis and perfusion difference, (B) demonstrates differences in arteriogenesis and perfusion. A solid regression line is fitted, while dotted line represents 95% confidence interval.

Figure 8:
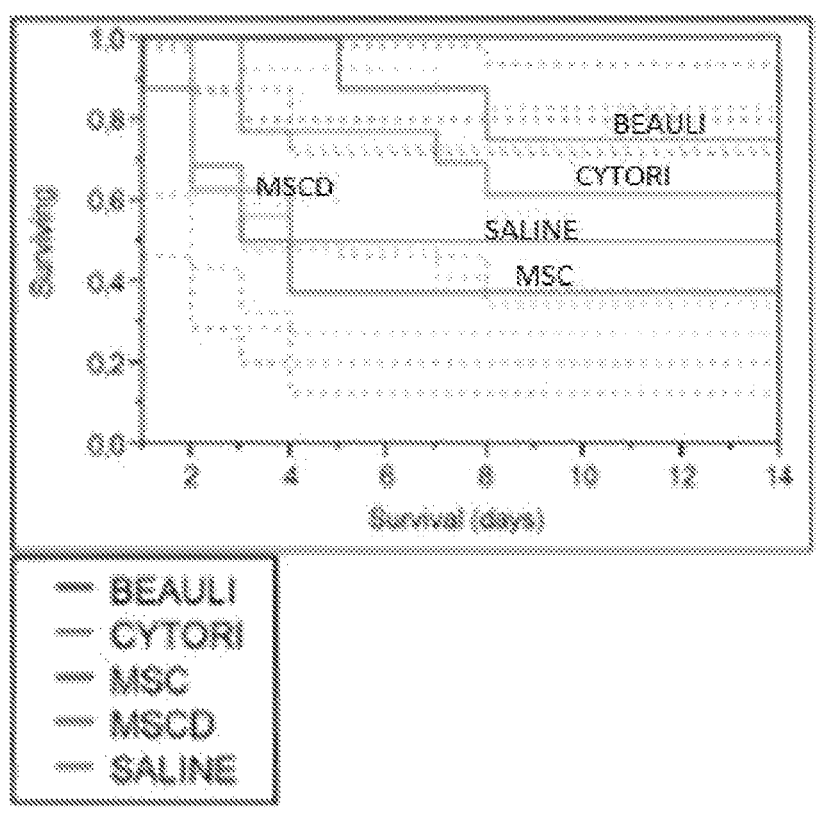

FIG. 8. Kaplan-Meier survival analysis of treatment groups. Dotted lines represent 95% confidence interval. BEAULI n=8, CYTORI n=13, MSC n=8, MSCD n=8 and SALINE n=16.

Figure 9:
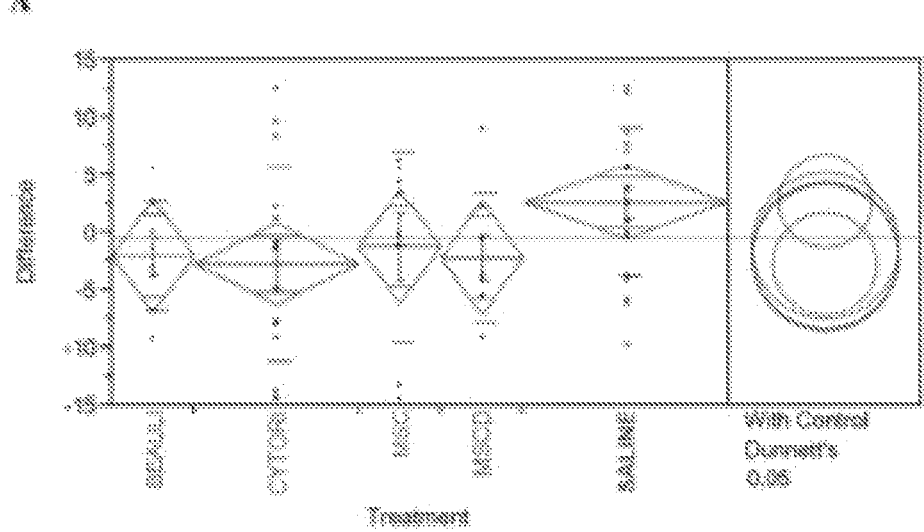
Figure 9:
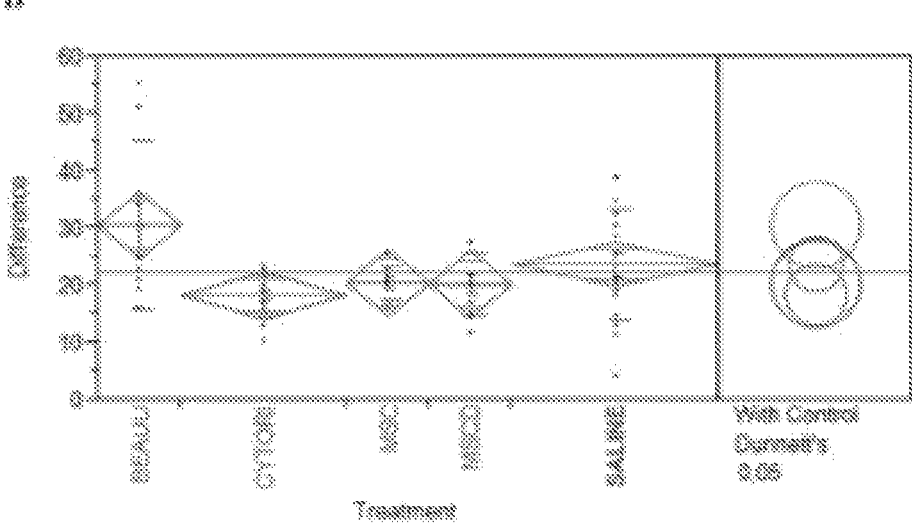
Figure 9:
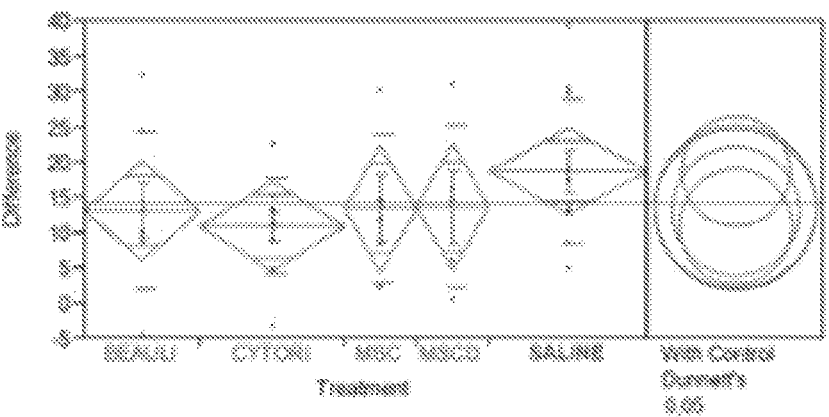
Figure 9:
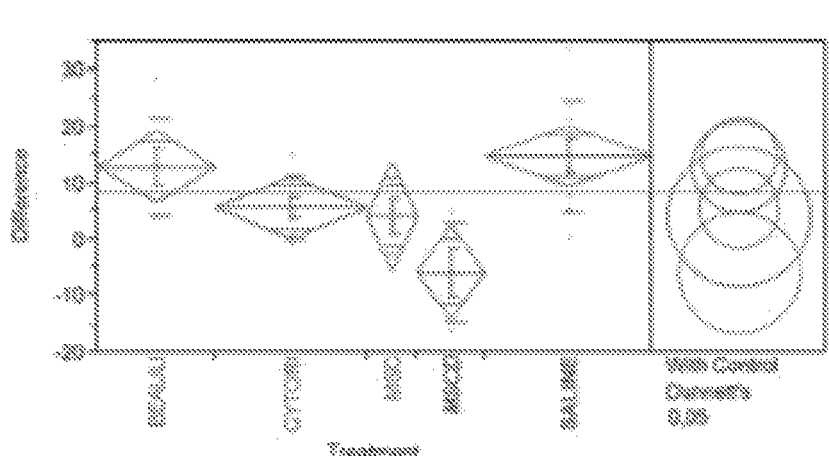
Figure 9:
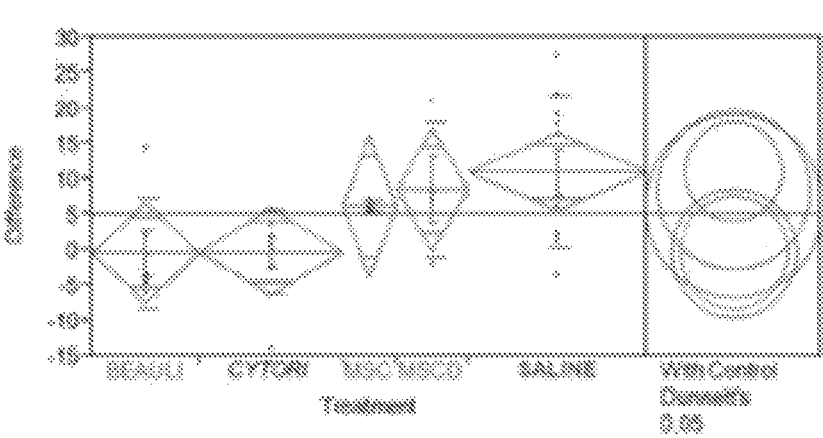

FIG. 9. One-way analysis of variance (ANOVA) of perfusion differences between treatment groups. (A) shows data before the operation, (B) demonstrates data right after the operation, (C) represents data 3 days after the operation, (D) shows data for 7 days after the operation, and (E) represents data for 14 days after the operation. BEAULI—group of operated and treated animals with lipoaspirate; CYTORI—group of animals treated with Cytori Cellution 800/CRS System—derived cells; MSC-mesenchymal stem cells isolated and expanded in laboratory; MSCD—mesenchymal stem cells treated with 10 μM metamizole (Analgin™); SALINE—control animals treated with 0.9% NaCl.

Figure 10:
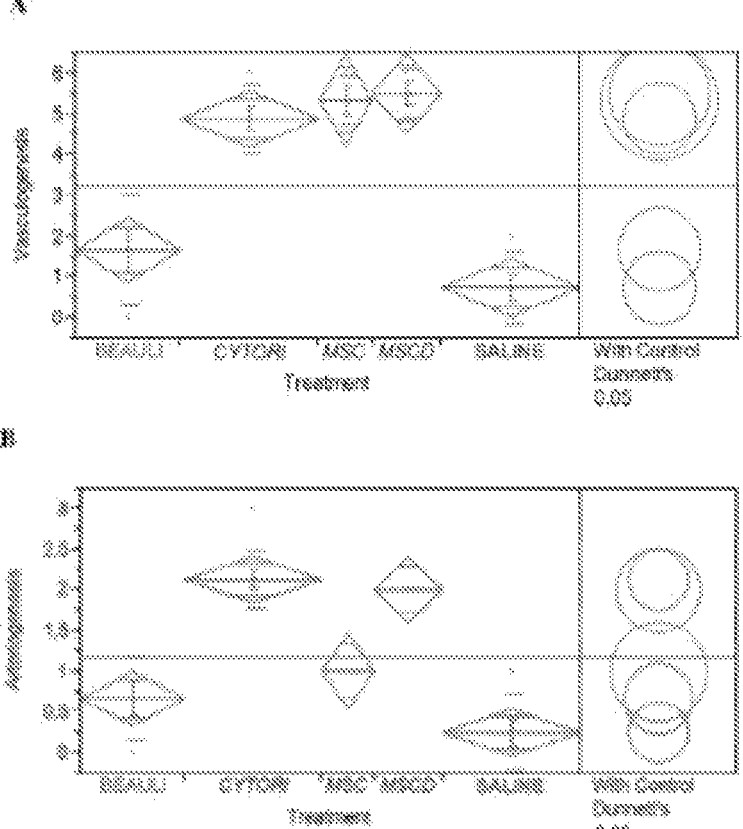

FIG. 10. One-way analysis of variance in vasculogenesis and arteriogenesis between treatment groups. (A) Vasculogenic and (B) arteriogenic analysis of variance. BEAULI—group of operated and treated animals with lipoaspirate; CYTORI—group of animals treated with Cytori Cellution 800/CRS System-derived cells; MSC—mesenchymal stem cells isolated and expanded in laboratory; MSCD—mesenchymal stem cells primed with 10 μM metamizole (Analgin™); SALINE—control animals treated with 0.9% NaCl.

Figure 11:
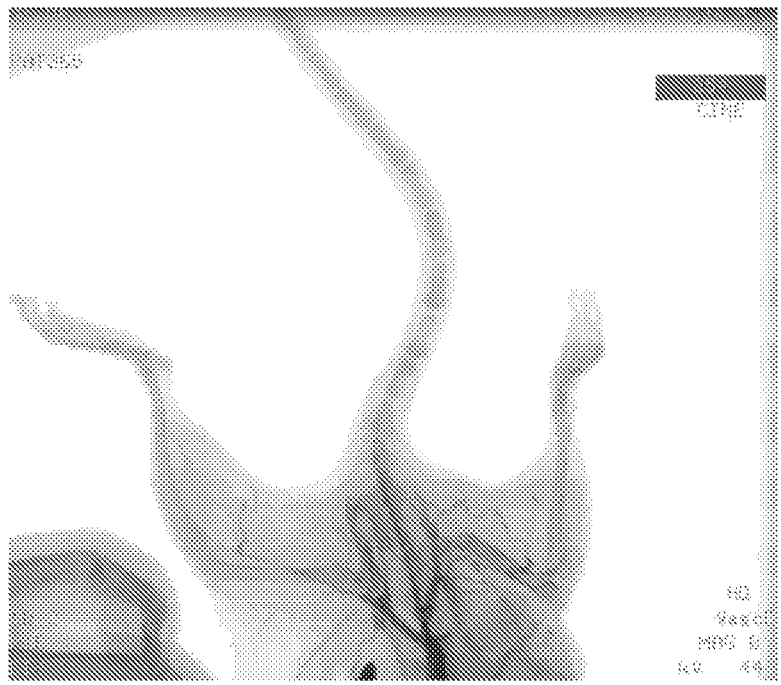

FIG. 11. Angiography from series of MSCD-treated animal.

Figure 12:
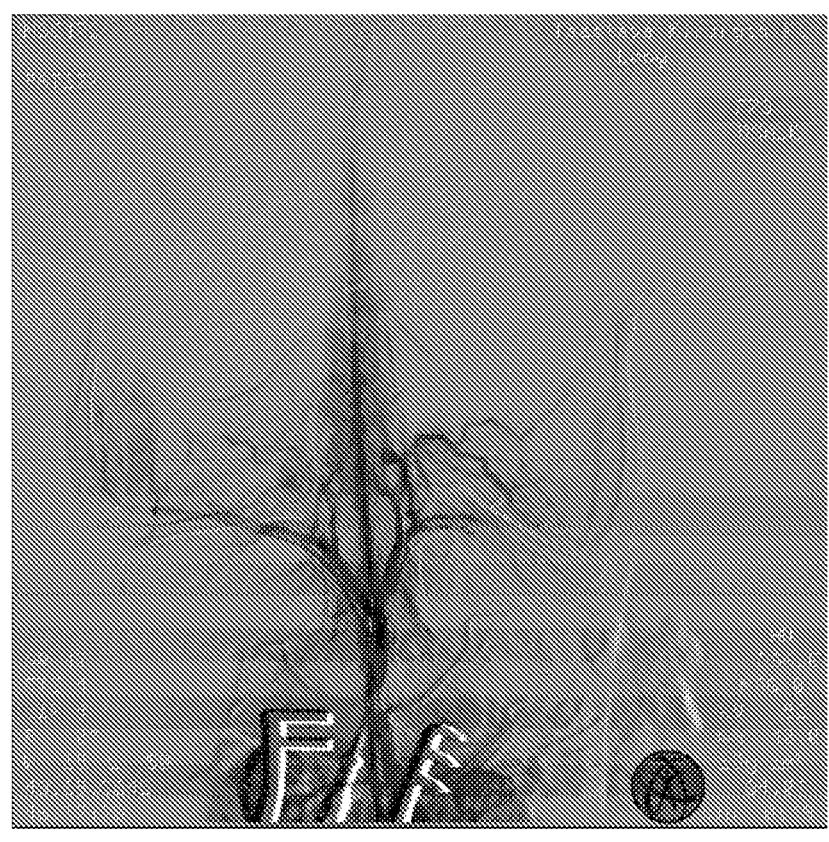

FIG. 12. Angiography from series of MSC-treated animal.

AIDs Affect Metabolic Activity and Cell Cycle Progression of MSCs

Analysis of effect of paracetamol (4.4 mM), diclofenac (10 µM), metamizole (Analgin™) (10 µM), ketoprofen (50 µM) and prednisolone (0.1 µM) on metabolic activity was conducted using a pool of AdMSCs isolated from at least three donors to reduce the effect of donor variation. Metabolic activity assay (WST-1) data showed that AIDs slightly change the metabolic activity of AdMSCs (FIG. 1). During the first 48 hours, all analyzed AIDs stimulated the metabolic activity of AdMSCs. Metamizole (Analgin™) treatment significantly stimulated cellular metabolism in first 24 hours, whereas all studied drugs demonstrated long-term suppressive effect on metabolic activity of AdMSCs (FIG. 1).

Effect of drugs on cell cycle changes measured by flow cytometry is shown in FIG. 2. In comparison with the non-treated control cells (G0/G1 phase-82%), the percentage of cells in G0/G1 phase was not significantly affected upon treatment with diclofenac (81%), ketoprofen (80%) and prednisolone (77%) (FIG. 2). The percentage of cells in G0/1 phase was lower in the cultures treated with metamizole (Analgin™) (65%) and paracetamol (71%), whereas the percentage of cells in G2/M cell cycle phase was increased in these cultures (FIG. 2). Obtained results show that metamizole (Analgin™) and paracetamol are the only studied drugs that affect cell cycle, since they accumulated the AdMSCs in the G2/M phase.

To conclude, all studied AIDs affected metabolic activity of AdMSCs, whereas metamizole (Analgin™) and paracetamol slightly altered also cell cycle progression.

AIDs Affect Expression of Angiogenic Factors

Numerous soluble factors produced by MSCs are involved in the regulation of angiogenesis and neovascularisation in vivo (Estrada et al., 2009). On the other hand, MSCs have been revealed to inhibit angiogenesis in certain conditions (Otsu et al., 2009). Also, trophic factors VEGF and bFGF have been shown to stimulate angiogenesis in ischemia treatments (Leung et al., 1989). The effect of the AIDs on expression of angiogenic factors in AdMSCs was analyzed. Different AIDs affected the expression of angio- VEGFA, HGF, bFGF and TEK mRNA expression (FIG. 3), diclofenac had no effect, paracetamol and prednisolone inhibited VEGFA and HGF expression. In addition, paracetamol induced bFGF, but strongly suppressed TEK expression, whereas prednisolone had opposite effect (FIG. 3).

Effect of AIDs on Expression of Immunomodulatory Factors

A number of inflammatory cytokines and chemokines secreted by MSCs are involved in the process of immunoregulation, thereby affecting immunocompetent cells. Quantitative differences in the levels of cytokines secreted by MSCs determine the local conditions of the microenvironment and induce anti-inflammatory reaction. Identification of inflammatory biomarkers profiles in response to MSCs therapy coupled with AIDs treatment could predict the consequences of such intervention for immunologic status in whole. The effect of AIDs treatments on inflammatory profile of AdMSCs at the protein and gene expression levels was analyzed.

Exposure of AdMSCs to paracetamol, diclofenac, metamizole (Analgin™), ketoprofen and prednisolone in standard culture conditions has minor effect on synthesis and secretion of immunomodulatory factors (Table 1). Only paracetamol resulted in significant reduction of IL6, CXCL8/IL8 and CCL2 levels in culture media compared to untreated cells.

To mimic inflammatory conditions, AdMSCs were exposed to lipopolysaccharide (LPS) prior to AIDs treatments. The levels of inflammatory cytokines IL6, CXCL8, CCL2 and IL1RN were increased following LPS treatment (Table 1). Then, LPS-treated AdMSCs were exposed to AIDs to study their effect on cytokines in inflammatory conditions.

Paracetamol and prednisolone significantly reduced levels of IL6 and CXCL8 in LPS-stimulated AdMSC cultures (Table 1). Inhibitory effect of metamizole (Analgin™) was detectable on CCL2 and IL1RN expression. On the contrary, ketoprofen and diclofenac stimulated the expression of IL6 and CXCL8 in LPS-stimulated AdMSC cultures. Interestingly, expose of AdMSCs to ketoprofen and diclofenac resulted in no effect on CCL2 levels.

TABLE 1

Secretion of inflammatory factors by AdMSCs in response to AIDs treatments. Concentrations in pg/ml of secreted IL6, CXCL8, CCL2 and IL1RN proteins were measured from the media of control, LPS-stimulated and AIDs-treated for 24 h AdMSCs by ELISA.

| MSCs treatments | concentration, pg/ml | | | |
|---|---|---|---|---|
| IL6 | | CXCL8 | CCL2 | IL-1RN |
| control | 40 ± 2 | 277 ± 12.7 | 96 ± 3.2 | 2.3 ± 0.03 |
| paracetamol | 0 | 11 ± 0.1 | 8 ± 0.4 | 11.0 ± 0.65 |
| diclofenac | 50 ± 1 | 284 ± 19.6 | 64 ± 8.4 | 14.5 ± 0.29 |
| metamizole (Analgin™) | 30 ± 1 | 341 ± 4.7 | 109 ± 3.2 | 3.9 ± 0.03 |
| ketoprofen | 10 ± 1 | 301 ± 0.3 | 165 ± 23.4 | 0 |
| prednisolone | 30 ± 2 | 35 ± 0.1 | 100 ± 12.2 | 7.3 ± 0.20 |
| control + LPS | 210 ± 22 | 2373 ± 109 | 461 ± 19.9 | 61 ± 18 |
| LPS + paracetamol | 90 ± 14 | 623 ± 41 | 270 ± 29.9 | 33 ± 9 |
| LPS + diclofenac | 390 ± 4 | 2807 ± 361 | 437 ± 16.8 | 17 ± 2 |
| LPS + metamizole (Analgin™) | 180 ± 29 | 1816 ± 121 | 313 ± 43.9 | 12 ± 1 |
| LPS + ketoprofen | 440 ± 143 | 2509 ± 68 | 451 ± 31.8 | 12 ± 0.5 |
| LPS + prednisolone | 50 ± 12 | 402 ± 51 | 314 ± 23.2 | 33 ± 2 | genic factors differently either stimulating or suppressing their expression. Treatment of AdMSCs with metamizole (Analgin™) and ketoprofen resulted in up-regulation of Effects of AIDs on mRNA expression of inflammatory cytokines in AdMSCs were analyzed using RT-qPCR technique. Analyses results were visualized as a heat map graph 7 8 using GENE-E platform (FIG. 4). Short-term treatment of AdMSCs by AIDs affected the expression of inflammatory cytokines. Exposure of AdMSCs to all studied AIDs for 24 hours significantly reduced levels of IL-1RN, IDO1, and chemokines CXCL9 and CXCL10, while IL4 mRNA expression was induced (FIG. 4). Expression of pro-inflammatory cytokines CCL2, CCL3, TNF, IL6, ILIA and ILIB was suppressed by ketoprofen and metamizole (Analgin™) treatments. NSAIDs treatments have opposite effects on expression of different TGFβ family members, whereas TGFβ1 and TGFβ3 were suppressed and TGFβ2 expression stimulated following paracetamol and diclofenac treatments (FIG. 4). Altogether, these data indicate that various AIDs differently altered AdMSCs transcriptome profile even in short-term treatments, stimulating or suppressing expression of specific inflammatory cytokines.

To study if the AIDs treatments of LPS-induced AdMSCs exhibit prolonged changes on cytokine levels, the effect of paracetamol and prednisolone on levels of cytokines in culture media was analyzed. Even a single treatment of LPS-induced AdMSCs in serum-deficient conditions affected significantly their cytokine profile (FIG. 5). Levels of CCL2, IL6 and IL-1RN were increased in the medium of the control untreated AdMSCs during 3-days. Activation of AdMSCs by LPS induced the expressions of CCL2, CXCL8, IL6 and IL-1RN in every analyzed time-point. Our results show that paracetamol treatment lowered the levels of CCL2 in LPS-treated cultures compared to control cultures and had no significant effects on CXCL8, IL6 and IL-1RN expression during the time (FIG. 5). In case of CCL2 and IL6 expressions, the effects of prednisolone treatment were opposite to the paracetamol, probably due to the implication of various mechanisms behind these drugs. Thus, prednisolone significantly stimulated the expression of CCL2 in all time-points, while inhibited IL-1RN and moderately induced levels of IL6 at 72 h after treatment (FIG. 5).

Effects of repeated AIDs treatments (48 and 72 h) on mRNA expression of cytokines in AdMSCs were analyzed using RT-qPCR technique. Differential expression of cytokine genes is represented as a heat map in FIG. 6. Analysis results showed different expression profile of cytokine genes between two time points. Upon exposure to various drugs, complex expression pattern of pro- and anti-inflammatory factors were observed. Although the expression of most pro-inflammatory cytokines such as IL1B, CXCL9, or CCL2 were down-regulated upon AIDs treatments, levels of some factors (TNF or MIF) were restored during the time, showing their dynamic regulation upon drug treatments. However, the stable induced expression of anti-inflammatory factors (IL4, TNFAIP6, IDO1) was not observed.

Altogether, these data indicate that expression of inflammatory factors can be significantly altered by various AIDs in a time-dependent manner.

Set Up of Animal Model of Muscle Ischemia Using Cytori Derived ADRCs as a Reference System The aim of the preclinical study was to assess conditions and cells that best promote neoangiogenesis and neoarteriogenesis by comparing differently isolated and conditionally manipulated human AdMSCs. These types of preclinical studies imply the use of a hind limb ischemia model (HLIM), where the restoration of the revascularization of ischemic muscle occurs due to the regenerative potential of administrated drugs (cells) but not by animal's own regeneration capability. This window-of-ischemia should last at least for 2-3 weeks. In the model, further, Hellingman model of HLIM that is well-suited for testing of AdMSCs for in vivo regeneration was successfully developed.

Treatment Suspension Preparation

BEAULI: Lipoaspirate obtained with use of body-jet (human med, routine clinical practice for treating soft tissue defects). Lipoaspirate is obtained with use of water-jet-assisted lipoaspiration. The harvested fat is gently separated from the remaining fluid with LipoCollector® or FillerCollector® and has been used immediately for fat transfer. This technique has been used as clinical standard for fat cells transfer.

CYTORI: Lipoaspirate obtained with water-jet-lipoaspiration was processed with Cytori Cellution 800/CRS System (Cytori Therapeutics INC.). Cytori Cellution-derived regenerative cells are as gold standard in regenerative medicine for enriching fat graft as well for improving angiogenesis in grafted areas. Cytori Cellution 800/CRS System uses lipoaspirate, digests with collagenase, washes and separates regenerative cells with centrifugation. Before injection the amount on nucleated cells was analyzed with cell counter. Average dosage of living nucleated cells were counted using Nucleocounter NC100 (Chemometec). Average count of living nucleated cells were $0.9 \times 10^6$ cells/ml.

MSC: Human AdMSCs were obtained from freshly isolated subcutaneous adipose tissue and characterized as previously reported (Lin et al., 2007). For each administration, a pool of AdMSCs from at least 3 individuals and passage number until 3 was grown in low glucose Dulbecco's modified Eagle's medium (DMEM-LG) (Gibco, Life Technologies, Carlsbad, CA, USA) supplemented with 10% fetal bovine serum (FBS) (PAA, Pasching, Austria) and 1% penicillin-streptomycin (PEST) (Life Technologies). Achieving about the 80-90% confluence, cells were collected and $2 \times 10^5$ cells were used per animal.

MSCD: AdMSCs were grown in standard culture conditions as described before until the 80-90% confluence, the medium was changed for DMEM-LG containing 1% FBS and 1% PEST at 12 h before the treatment, stimulated with LPS (0.1 ug/ml; Sigma-Aldrich, Steinheim, Germany) for 2 hours, intensively washed with phosphate buffered saline (PBS), and treated with metamizole (Analgin™) (10 μM) for 24 hours. Cells were collected and $2 \times 10^5$ cells were used per animal.

SALINE: In control series rats were treated with saline (0.9% NaCl) injection.

Animal Studies

For preclinical animal studies, four different treatments were tested—BEAULI, CYTORI, MSC and MSCD. In each series, 11 animals were operated—8 treated with different cells injected to the gastrocnemius muscle, and 3 control animals treated with saline. Additionally, separate control series of 6 animals were operated.

All animal experiments were designed in accordance with European Directive 2010/63/EU, local legislation for animal protection (LoKS) and approved by Ethic Committee of Estonian Ministry of Agriculture (now Ministry of Rural Affairs).

Female Sprague-Dawley (SD) rats were housed under standard animal facility conditions (2-4 animals per cage in temperature (22±2° C.) and humidity (55±10%) controlled room with 12 h: 12 h light: dark cycle). Animals were given ad libitum access to standard maintenance rodent diet and water.

In our series, adult rats (4±1 months old (n=50) and in one series 12 to 13 months old (n=11)) were used. See section Statistical analysis for details of group number and sizes.

Surgical Method

Animals were operated in supine position under general anesthesia (ketamine (100 mg/ml; Vetoquinol, France) mixture with medetomidine (1 mg/ml; Syva, Spain) 75 mg/kg and 0.5 mg/kg respectively given intraperitoneally). Incision was made on right limb. External iliac artery, femoral arteries, popliteal artery and all side branches were exposed. Varied sizes of tantalum micro clips were used to occlude arteries and side branches. Tantalum micro clips are good markers in time of angiographic study. Electro cautery was used to resect iliac and femoral arteries and veins. 0.4 ml of cell suspension in treatment groups or 0.9% saline in control groups were injected in animal's gastrocnemius muscle. Skin was closed with interrupted sutures and secured with skin staplers. Anesthesia was reversed by atipamezole (5 mg/ml; Syva, Spain) 1 mg/kg subcutaneous injection. Animals were weighted daily, monitored for signs of pain and given analgesics during recovery period (buprenorphine (0.3 mg/ml; Richterpharma AG, Austria) 0.01-0.03 mg/kg every 6-12 hours as needed during minimally first three days combined with ketoprofen (10 mg/ml; Merial, France) 5 mg/kg every 24 hours as needed during minimally five days. Euthanasia was applied when weight loss exceeded 20% or cumulative signs of severe pain and distress or moribund condition observed.

Laser Doppler Blood Perfusion Measurements

Animals were under general anesthesia (deep surgical at days of surgical intervention and half-dose for perfusion measurements only). In measurement area hair were removed using electric shaver and hair removal cream. Animals were placed on heated temperature-controlled surface to keep them at temperature 37° C. for 5 minutes. For measurements, PeriCam PSI (Perimed AB) was used. Measuring distance was 15 cm. Measurements were performed on heated and temperature-controlled surface. On both limbs, Region of Interest (ROI) was selected. Measurements were performed before the surgery, right after the surgery, and 3, 7 and 14 days after the surgery. As different animals differ in perfusion despite of standard condition, difference and comparative difference between operated and control limb on same animal were used for analysis.

Angiography

Angiography was performed on the 14th day after the surgery. Animals were under the general anesthesia, on supine position, on heated and temperature-controlled surface. Midline incision was performed in abdominal wall, where abdominal aorta was exposed. MicroSlide kit (Galt Medical Corp) together with contrast medium Omnipaque 300 were used for aortic cannulation. Digital Subtraction Angiography was performed with Ziehm Vision RFD, 20 KW (Ziehm Imaging GmbH).

The angiography results were analyzed by two vascular surgeons who did not know the study groups. In analysis, the total amount of detectable vessels was counted, as well as the count of curled vessels to see neoarteriogenesis separately from vasculogenesis.

Statistical Analysis

Statistical analysis was performed by Microsoft Excel and JMP10.0 SAS statistical analysis software. Linear regression was used to analyze the relation between vasculo- or arteriogenesis and perfusion. Kaplan-Meier method was used to analyze survival, and one-way analysis of variance (ANOVA) was used to compare mean differences of perfusion and mean value of new blood vessels between different treatment groups. For mean comparisons, Dunnett's post hoc tests were used to compare the treatment groups with saline control group. If there was no change (less than 3 perfusion units) in perfusion difference before and after the operation, the modeling of ischemia was considered to be unsuccessful in the animal and all these cases (3 saline-treated control animals) were excluded from the statistical analysis. There were two series of CYTORI treated animals—in one of them the older rats were used, but as there were no statistically significant differences in any measurements between older and younger CYTORI treated rats, these two series of 8 animals were considered as one treatment group (n=16).

Results

Correlation analysis between laser doppler blood perfusion measurements and angiography findings are shown in FIG. 7.

There is statistically significant negative correlation between perfusion difference (perfusion in control leg-perfusion in operated leg) measured 7 days after the operation and both vasculo- and arteriogenesis (angiography done 14 days after the surgery). R=0.51; p-value 0.0031 for vasculogenesis and R=0.46; p-value 0.0095 for arteriogenesis respectively, n=31 for both. As expected, the correlation analysis shows that if there is better perfusion in operated leg, there is also bigger number of new blood vessels.

Survival analysis is shown in FIG. 8.

There is no statistically significant difference in survival between different treatment groups.

Analysis of perfusion differences is shown in FIG. 9.

As seen in FIG. 9, there are no statistically significant differences between the groups before, right after and 3 days after the operation. After 7 days, there is statistically significant improvement in MSCD, and after 14 days in CYTORI group compared to saline treated control with P-values 0,0008 and 0.0322, respectively. The analysis showed that animals treated with MSCs primed with metamizole (Analgin™) (study group MSCD) had faster recovery of blood perfusion than other groups already on seventh day after the surgery (P-value 0,0008). The difference between MSC and SALINE groups statistically is not significant, probably because of small MSC group size (only 3 animals out of 8 survived until day 7).

Analysis of vasculogenesis between different cell treatment groups is shown in FIG. 10.

For CYTORI, MSC and MSCD treated animals, significantly better neoangiogenesis was observed compared to the saline control group animals (P-values are less than 0,0001 for all groups for both vasculogenesis and arteriogenesis; while for arteriogenic analysis of MSC group P-value is 0,034).

Two vascular surgeons, who were blinded to the treatment, analyzed the results of angiography. In analysis, total amount of all detectable vessels and curled vessels amount (fraction of all the vessels) were counted to evaluate overall vasculogenesis and neoarteriogenesis respectively. From angiography images, it is clearly seen that for MSC and MSCD-treated animals were observed effective neoarteriogenesis and neoangiogenesis on the operated limb.

The invention claimed is:

1. A method for promoting angiogenesis in a limb of a human having restricted blood supply, the method comprising:

(i) treating human adipose-derived mesenchymal stem cells (AdMSCs) with lipopolysaccharide (LPS) to heighten levels of inflammatory cytokines in the AdMSCs thereby producing LPS treated AdMSCs, (ii) treating the LPS treated AdMSCs with metamizole to suppress expression of pro-inflammatory cytokines CCL2, CCL3, TNF, IL6, IL1A, and IL1B and thereby producing metamizole treated AdMSCs, and (iii) intramuscularly administering to the limb of the human the metamizole treated AdMSCs in an amount effective to stimulate formation of new blood vessels in the limb of the human.

2. The methods according to claim 1, wherein the metamizole treated AdMSCs are injected into a muscle of the subject in a dose of 1 million cells per kg of the subject.

3. The method according to claim 1, wherein the metamizole treated AdMSCs are administered to the subject in an amount of 0.75-1.5 million cells per kg of body weight of the subject.

4. The method according to claim 3, wherein the AdMSCs are produced by a process comprising the following steps:

(i) collecting fat tissue (ii) separating mesenchymal stem cells (MSCs) from the fat tissue to produce adipose-derived mesenchymal stem cells (AdMSCs), and (iii) expanding the AdMSCs.

5. The method according to claim 1, wherein in step (i) the AdMSCs are stimulated with 0.1 µg/ml of the LPS for 2 hours.

6. The method according to claim 5, wherein in step (ii) the LPS treated AdMSCs are contacted with 10 µM of the metamizole for 24 hours.

\* \* \* \* \*